US010626381B2

(12) United States Patent
Reyes Sosa et al.

(10) Patent No.: US 10,626,381 B2
(45) Date of Patent: Apr. 21, 2020

(54) CELLULOLYTIC COMPOSITIONS COMPRISING MONOOXYGENASE POLYSACCHARIDE ENZYMES WITH IMPROVED ACTIVITY

(71) Applicant: ABENGOA BIOENERGÍA NUEVAS TECNOLOGÍAS, S. A., Seville (ES)

(72) Inventors: Francisco Manuel Reyes Sosa, Seville (ES); Bruno Díez García, Seville (ES); Noelia Valbuena Crespo, Seville (ES); Antonio Javier Moreno Pérez, Seville (ES); Dolores Pérez Gómez, Seville (ES); Ana Isabel Platero Gómez, Seville (ES); Lucía Martín Pérez, Seville (ES); Sandra Gavaldá Martín, Seville (ES); Laura Viñas De La Cruz, Valencia (ES); Laura Sánchez Zamorano, Seville (ES); Consolación Álvarez Núñez, Seville (ES); María de los Angeles Bermúdez Alcántara, Seville (ES); Javier Rocha Martín, Seville (ES); Laura Ledesma García, Seville (ES); Juan Luis Ramos Martín, Seville (ES)

(73) Assignee: ABENGOA BIOENERGÍA NUEVAS TECNOLOGÍAS, S. A., Seville (ES)

( * ) Notice: Subject to any disclaimer, the term of this patent is extended or adjusted under 35 U.S.C. 154(b) by 0 days.

(21) Appl. No.: 15/739,679

(22) PCT Filed: Jun. 23, 2015

(86) PCT No.: PCT/ES2015/070485
§ 371 (c)(1),
(2) Date: Dec. 22, 2017

(87) PCT Pub. No.: WO2016/207448
PCT Pub. Date: Dec. 29, 2016

(65) Prior Publication Data
US 2018/0187167 A1 Jul. 5, 2018

(51) Int. Cl.
| | | |
|---|---|---|
| *C12P 7/10* | (2006.01) | |
| *C12N 9/04* | (2006.01) | |
| *C12N 9/02* | (2006.01) | |
| *C12P 19/02* | (2006.01) | |
| *C12P 19/14* | (2006.01) | |
| *C12N 9/24* | (2006.01) | |
| *C12N 9/96* | (2006.01) | |
| *C12N 1/14* | (2006.01) | |

(52) U.S. Cl.
CPC ......... *C12N 9/0069* (2013.01); *C12N 9/2402* (2013.01); *C12N 9/96* (2013.01); *C12P 7/10* (2013.01); *C12P 19/02* (2013.01); *C12P 19/14* (2013.01); *C12N 1/14* (2013.01); *C12Y 114/13025* (2013.01); *Y02E 50/16* (2013.01)

(58) Field of Classification Search
CPC .... C12N 9/42; C12N 9/24; C12N 9/14; C12P 7/14; C12P 7/06
See application file for complete search history.

(56) References Cited

U.S. PATENT DOCUMENTS

2014/0127771 A1  5/2014  Johansen et al.

FOREIGN PATENT DOCUMENTS

| ES | 2542621 | 8/2015 |
|---|---|---|
| WO | WO-2012061517 | 5/2012 |
| WO | WO-2012138772 | 10/2012 |
| WO | WO-2013028701 | 2/2013 |
| WO | WO-2013048661 | 4/2013 |

OTHER PUBLICATIONS

International Search Report dated Mar. 10, 2016, PCT Application No. PCT/ES2015/070485.
Baldrian, et al., "Degradation of cellulose by basidiomycetous fungi", FEMS Microbiol Rev, vol. 32, 2008, 501-521.
Harris, et al., "Stimulation of Lignocellulosic Biomass Hydrolysis by Proteins of Glycoside Hydrolase Family 61: Structure and Function of a Large, Enigmatic Family", Biochemistry, 49, 2010, 3305-3316.
Kitt, et al., "Production of four Neurospora crassa lytic polysaccharide monooxygenases in Pichia pastoris monitored by a fluorimetric assay", Biotechnology for Biofuels, 5:79, 2012, 1-13.
Kuhad, et al., "Microbial Cellulases and Their Industrial Applications", Enzyme Research, vol. 2011, Article ID 280696, 2011, 1-10.
Langston, et al., "Oxidoreductive Cellulose Depolymerization by the Enzymes Cellobiose Dehydrogenase and Glycoside Hydrolase 61", Applied and Environmental Microbiology, vol. 77, No. 19, Oct. 2011, 7007-7015.

(Continued)

*Primary Examiner* — Maryam Monshipouri
(74) *Attorney, Agent, or Firm* — Womble Bond Dickinson (US) LLP

(57) ABSTRACT

The invention refers to methods and compositions for stabilizing and increasing the activity of enzymatic mixtures comprising GH61 (PMO or polysaccharide monooxigenase) polypeptides used for the degradation of cellulosic material during the saccharification step of biofuel production processes. This improvement is achieved by the addition of a nickel cation to said enzymatic mixtures before and/or during the saccharification step. Thus, the invention provides compositions comprising PMOs, cellulolytic enzymes and a nickel cation, as well as methods for preparing said compositions and methods for producing fermentable sugars and bioproducts, preferably bioethanol, from cellulosic biomass in which said compositions are used.

20 Claims, 5 Drawing Sheets
Specification includes a Sequence Listing.

(56) References Cited

OTHER PUBLICATIONS

Lee, et al., "Substrate-Enzyme Interactions in Cellulase Systems", Bioresource Technology 58, 1996, 163-169.
Mosier, et al., "Features of promising technologies for pretreatment of lignocellulosic biomass", Bioresource Technology 96, 2005, 673-686.

CELLULOLYTIC COMPOSITIONS COMPRISING MONOOXYGENASE POLYSACCHARIDE ENZYMES WITH IMPROVED ACTIVITY

CROSS-REFERENCE TO RELATED APPLICATIONS

The present patent application is a national phase application of International Application No. PCT/ES2015/070485, filed Jun. 23, 2015, the disclosure of which is incorporated herein by reference.

INCORPORATION BY REFERENCE

An electronic copy of the Sequence Listing entitled "Sequence_Listing.txt" and having a file size of 8,000 bytes is incorporated herein by reference. This Sequence Listing consists of [SEQ ID NOs: 1-3].

The invention relates to the field of bioproducts, more particularly to the improvement of enzymatic mixtures comprising polypeptides with polysaccharide monooxygenase activity and their use for the production of fermentable sugars from cellulosic biomass during processes for the production of bioproducts, such as bioethanol.

BACKGROUND

Plant biomass provides an abundant source of potential energy in the form of carbohydrates that can be used in numerous industrial and agricultural processes and, therefore, is an important renewable source for generating fermentable sugars. Fermentation of these sugars can produce valuable commercial end products such as biofuels and biochemicals.

Although fermentation of sugars to ethanol is relatively straightforward, efficient conversion of cellulosic biomass to fermentable sugars such as glucose is more challenging. The huge potential energy of large amounts of carbohydrates in plant biomass is not sufficiently used because the sugars form part of complex polymers (polysaccharides, such as cellulose and hemicellulose) and, therefore, are not easily accessible for fermentation. Thus, cellulose can be pre-treated mechanically, chemically, enzymatically or in other ways to increase its susceptibility to hydrolysis. After this pre-treatment process, there is a saccharification or hydrolysis stage consisting of an enzymatic process in which complex carbohydrates (such as starch or cellulose) are hydrolysed into their monosaccharide components. The goal of any saccharification technology therefore is to change or remove structural and compositional obstacles in order to improve the rate of enzymatic hydrolysis and increase the yield of fermentable sugars obtained from cellulose or hemicellulose (N. Mosier et al., 2005, *Bioresource Technology* 96, 673-686). After the saccharification stage, the fermentation process is performed. Therefore, the higher the amount of complex sugars remaining at the end of the hydrolytic process, the lower the yield in ethanol production at the end of the fermentation process. Thus, an area of research directed at reducing costs and improving the yield of biofuel production processes is focussed on improving the technical efficiency of hydrolytic enzymes, or generally on improving the efficiency of enzyme cocktails used to generate fermentable sugars from biomass.

It has been shown that individual enzymes are only capable of partially digesting cellulose and hemicellulose and therefore the combined action of different classes of enzymes is required to complete their conversion into monomeric sugars. Many more enzymes are required for digesting hemicellulose to monomeric sugars that for cellulose, including enzymes with xylanase, beta-xylosidase, arabinofuranosidase, mannanase, galactosidase and glucuronidase activity. Other enzymes without glycosyl hydrolase activity can also be involved such as acetyl xylan esterase and ferulic acid esterase. Therefore, enzymatic hydrolysis of polysaccharides for their conversion to soluble sugars and, finally, to monomers such as xylose, glucose and other pentoses and hexoses are catalysed by various enzymes that together are called "cellulases". Cellulases are multienzyme complexes comprising at least three main components, endo-β-glucanase (EC 3.2.1.4), exo-β-glucanase or cellobiohydrolase (EC 3.2.1.9.1) and β-glucosidase (EC 3.2.1.21), and it has been shown that they act synergistically in the hydrolysis of cellulose (Woodward, J. 1991, *Bioresource Technology* Vol 36, pp. 67-75).

Microbial cellulases have become focal biocatalysts because of their complex nature and their extensive industrial applications (Kuhad R. C. et al., 2011, *Enzyme Research*, Article ID 280696). Recently, considerable attention has been paid to current knowledge on the production of cellulases and the challenges in cellulases researching have been focus especially in obtaining cellulases with higher activity and improved properties.

On the other hand, glycosyl hydrolase proteins of family 61 (GH61) have been known for over 20 years. These GH61 proteins are accessory proteins that contribute to cellulose degradation. The fact that these enzymes act by direct oxidation of cellulose, rather than by hydrolysis, has led to their current name: Cu dependent polysaccharide monooxygenases (Polysaccharide Monooxygenase; PMOs). Compared to other cellulolytic enzymes, PMOs are relatively small proteins with typical molecular weights of between 20 and 50 kDa (Baldrian and Valaskova 2008, *FEMS Microbiology Reviews* 32: 501-521; Harris et al., 2010, *Biochemistry* 49: 3305-3316). These proteins require two oxygen molecules to cause product breakdown and oxidation. One of these molecules derives from water, the other enters the reaction in the form of molecular oxygen, which is necessary for direct oxidation of the substrate. Therefore, members of this enzyme family act as Cu monooxygenases that catalyse the breakdown of cellulose by an oxidative mechanism, releasing cellodextrins (Langston et al., 2011, *Applied and Environmental Microbiology* 77: 7007-7015).

The hydrolytic efficiency of a multi-enzyme complex in the saccharification process of cellulosic material depends both on the properties of the individual enzymes and on the proportion of each enzyme present in the complex. Therefore, in the context of biofuel production processes, enzyme cocktails need to be designed with improved individual activities. Specifically, it would be an advantage in the art to improve the activity and stability of PMO polypeptides. In this sense several publications have proposed the supplementation of the enzymatic mixtures containing cellulases and PMOs with copper, which is a cofactor of PMOs, to increase the activity and stability of these enzymes (US2014127771, WO2012138772).

In summary, the use of enzymatic mixtures containing PMO polypeptides with improved activity and/or stability during the saccharification or hydrolysis stage of cellulosic biomass will lead to an improvement in the yield of this stage through an increase in the amount of final fermentable sugars. Later, these sugars can be fermented to produce biofuels such as bioethanol, so this would ultimately increase the efficiency and profitability of the whole biofuel production process.

DESCRIPTION OF THE INVENTION

The present invention relates to methods and compositions for stabilizing and increasing the activity of enzymatic mixtures comprising GH61 (or PMO) polypeptides used for the degradation of cellulosic material during the saccharification step of biofuel production processes. This improvement is achieved by the presence or addition of a nickel cation to said enzymatic mixtures before and/or during the saccharification step.

Examples shown below evidence that the presence of nickel in enzymatic mixtures comprising PMOs and cellulolytic enzymes produced by the C1 strain of *Myceliophthora thermophila* resulted in a higher concentration of fermentable sugars (mainly glucose) released in a biomass saccharification process compared to an enzymatic mixture comprising the same enzymes but lacking nickel (FIGS. 1, 2, 3 and 5). This indicates that nickel presence leads to an increase in the cellulolytic activity of the enzymatic cocktails by means of an increase in the activity of the PMOs included in them.

Examples also show that the presence of nickel in said enzymatic mixtures leads to a higher yield in fermentable sugars (mainly glucose) released in a biomass saccharification process compared to the presence of other divalent metals, such as $Mg^{2+}$ or $Mn^{2+}$ (FIG. 5).

Furthermore, FIG. 4 shows that PMOs are more stable in the presence of nickel than in the absence, which contributes to the improvement of their activity in the enzymatic mixture. In addition, the nickel addition does not affect the thermostability of other celulolytic enzymes.

This invention therefore shows that nickel presence in enzyme cocktails comprising GH61 or PMOs polypeptides contributes to improve the yield of the hydrolytic process of the cellulosic biomass wherein these cocktails are used. This consequently leads to the improvement of biofuel production.

Therefore, a first aspect of this invention refers to a composition comprising at least one polysaccharide monooxygenase enzyme (PMO) and a nickel cation. Hereinafter, this composition will be referred to as "composition of the invention".

In a preferred embodiment of the composition of the invention, the nickel cation is present at a concentration of more than 0.0001 mM and less than 50 mM, preferably between 0.001 and 20 mM, more preferably between 0.001 and 5 mM, even more preferably between 0.05 and 5 mM and even more preferably between 0.05 and 0.5 mM. As shown in the examples below, a nickel concentration between 0.05 and 0.5 mM renders the highest glucose yield by the enzymatic mixture over cellulosic biomass compared to other nickel concentrations outside this range. Thus, this range for nickel concentrations in the composition of the invention is the most preferred one. In an even more preferred embodiment, the nickel concentration is between 0.075 and 0.125 mM, even more preferably the nickel concentration is 0.125 mM.

In a more preferred embodiment of the composition of the invention, the nickel cation is a divalent cation. The divalent nickel cation is preferably present as a soluble salt, for example, a chlorate, chloride, chromate, acetate, citrate, fluoride, formate, iodide, nitrate, oxalate, perchlorate, selenate, or sulphate salt, or as an insoluble salt, for example, a carbonate, hydroxide, oxide, phosphate, pyrophosphate, or sulfide salt.

More preferably the nickel cation is in the form of a salt. Even more preferably, the nickel salt is selected from nickel sulphate, nickel chloride, nickel nitrate, nickel acetate or nickel hydroxide, or any combination thereof.

The nickel cation may be added to the composition of the invention and/or may be already present in the bioreactor wherein the biomass hydrolysis is being performed with the enzymatic composition, since cellulosic biomass can comprise a number of divalent metal cations, including Ni. Therefore, cellulosic biomass may be, in part or wholly, a source of the nickel cation. This nickel cation may be soluble or insoluble. However, the nickel cation may be unavailable in solution because, for example, it is complexed with a component of the cellulosic biomass. For this reason, addition or supplementation of the composition of the invention with a nickel cation may be needed.

The terms "polysaccharide monooxygenase", "PMO", "cellulolytic enhancing activity polypeptide", "glycosyl hydrolase family 61" or "GH61" refer to an enzyme with GH61 or PMO activity, which catalyzes the enhancement of the hydrolysis of a cellulosic material by enzymes having cellulolytic activity. When it is included in a saccharification reaction (for example that in which endoglucanases, beta-glucosidases and cellobiohydrolases are used) results in a higher amount (higher yield) of one or more soluble sugars (for example glucose) released compared to the saccharification reaction performed under the same conditions but in the absence of the GH61 protein. PMO activity can be determined by, for example, indirect oxidative assays that show colorimetrically the phenomenon of electron transfer using various electron donor and acceptor compounds (Kitt et al., 2012, *Biotechnology for Biofuels Vol.* 5:79, pp. 1-13). On the other hand, the efficiency on biomass could be measured, for example, by combining the PMO polypeptide with cellulase enzymes in a saccharification reaction and determining if there is an increase in the glucose yield compared to the same saccharification reaction performed in the absence of this polypeptide.

PMO polypeptides may be obtained, but without limitation, from a filamentous fungus such as *Acremonium, Aspergillus, Aureobasidium, Cryptococcus, Gibberella, Filibasidium, Fusarium, Humicola, Magnaporthe, Mucor, Neocallimastix, Neurospora, Paecilomyces, Penicillium, Piromyces, Schizophyllum, Talaromyces, Thermoascus, Thielavia, Tolypocladium, Trichoderma* or *Myceliophthora*. Examples of PMOs that may be used, but without limitation, in the present invention are those described in Appli. Number ES201430155 and Publi. Number WO2013048661A1, WO2012061517A1 and WO2013028701A1. In a more preferred embodiment, the PMO is a PMO from *Myceliophthora thermophila, Gibberella zeae, Humicola insolens, Humicola lanuginosa, Mucor miehei, Neurospora crassa, Penicillium purpurogenum, Talaromyces magnefei, Trichoderma harzianum, Trichoderma koningii, Trichoderma longibrachiatum, Trichoderma reesei,* or *Trichoderma viride*. In an even more preferred embodiment of the composition of the invention, the PMO enzyme is a *Myceliophthora thermophila* or a *Penicillium* sp. PMO, more preferably the PMO is a *Myceliophthora thermophila* PMO, more preferably the PMO enzyme is selected from PMO1, PMO2, PMO3 or any combination thereof. In a more preferred embodiment, the composition of the invention comprises PMO1 and PMO2.

It is understood that for the aforementioned species, the invention encompasses the perfect and imperfect states, and other taxonomic equivalents, for example the anamorphic, with respect to the name of the species by which they are known. Experts in the field will easily recognise the identity of appropriate equivalents. For example, *Myceliophthora thermophila* is equivalent to *Chrysosporium lucknowense*.

In a more preferred embodiment, PMO1 is a polypeptide comprising the SEQ ID NO: 1, PMO2 is a polypeptide comprising the SEQ ID NO: 2 and PMO3 is a polypeptide comprising the SEQ ID NO: 3.

PMO enzyme/s comprised in the composition of the invention may be isolated, preferably from *M. thermophila*, or produced recombinantly. PMO enzyme/s may be synthesised, for example but without limitation, in vitro. For example, via solid phase peptide synthesis or via recombinant DNA approaches. PMO enzyme/s can be produced recombinantly, not only directly but also as a fusion polypeptide together with an homologous or heterologous polypeptide, that can contain, for example but without limitation, a signal sequence or other polypeptide that has a protease cleavage site, for example but without limitation, at the N-terminal end of the mature protein or of the polypeptide.

The composition of the invention may further comprise other enzymatic activities such as aminopeptidase, amylase, carbohydrase, carboxypeptidase, catalase, cellulase, such as endoglucanases, beta-glucosidases and/or cellobiohydrolase activities; chitinase, cutinase, cyclodextrin glycosyltransferase, deoxyribonuclease, esterase, alpha-galactosidase, beta-galactosidase, glucoamylase, alpha-glucosidase, haloperoxidase, invertase, laccase, lipase, mannosidase, oxidase, reductase, pectinolytic enzyme, peptidoglutaminase, peroxidase, phytase, polyphenoloxidase, protease, proteolytic enzymes, ribonuclease, transglutaminase or xylanase, or any combination of these. The additional enzyme(s) may be produced, for example, by a microorganism belonging to the genus *Acremonium, Agaricus, Alternaria, Aspergillus* such as *Aspergillus aculeatus, Aspergillus awamori, Aspergillus fumigatus, Aspergillus foetidus, Aspergillus japonicus, Aspergillus nidulans, Aspergillus niger* or *Aspergillus oryzae; Aureobasidium, Bjerkandera* such as *Bjerkandera adusta, Botryosphaeria, Candida, Ceriporiopsis* such as *Ceriporiopsis aneirina, Ceriporiopsis caregiea, Ceriporiopsis gilvescens, Ceriporiopsis pannocinta, Ceriporiopsis rivulosa, Ceriporiopsis subrufa* or *Ceriporiopsis subvermispora, Chaetomidium, Chrysosporium, Claviceps, Cochliobolus, Coprinopsis, Coprinus* such as *Coprinus cinereus, Coptotermes, Coriolus* such as *Coriolus hirsutus, Corynascus, Cryphonectria, Cryptococcus, Diplodia, Exidia, Filibasidium, Fusarium* such as *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium pseudograminearum, Fusarium reticulatum, Fusarium roseum, Fusarium sambucinum, Fusarium sarcochroum, Fusarium sulphureum, Fusarium toruloseum, Fusarium trichothecioides* or *Fusarium venenatum; Gibberella* such as *Gibberella zeae; Holomastigotoides, Humicola* such as *Humicola insolens* or *Humicola lanuginosa; Irpex, Kluyveromyces, Lentinula, Leptospaeria, Magnaporthe, Melanocarpus, Meripilus, Mucor* such as *Mucor miehei, Myceliophthora* such as *Myceliophthora thermophila, Neocallimastix, Neurospora* such as *Neurospora crassa, Paecilomyces, Penicillium* such as *Penicillium purpurogenum, Phanerochaete* such as *Phanerochaete chrysosporium, Phlebia* such as *Phlebia radiata, Pichia, Piromyces, Pleurotus* such as *Pleurotus eryngii, Poitrasia, Pseudoplectania, Pseudotrichonympha, Rhizomucor, Saccharomyces, Schizosaccharomyces, Schizophyllum, Scytalidium, Talaromyces, Thermoascus, Thielavia* such as *Thielavia terrestris, Tolypocladium, Trametes* such as *Trametes villosa* or *Trametes versicolor, Trichoderma* such as *Trichoderma harzianum, Trichoderma koningii, Trichoderma longibrachiatum, Trichoderma reesei* or *Trichoderma viride, Trichophaea, Verticillium, Volvariella, Xylaria* or *Yarrowia*.

In a more preferred embodiment, the composition of the invention further comprises cellulolytic enzymes. The term "cellulolytic enzymes" also known as "cellulases" refers to a class of enzymes able to hydrolyse cellulose (β-1,4-glucan or β-D-glycosidic bonds) or hemicellulose to shorter oligosaccharides, cellobiose and/or glucose. Examples of cellulolytic enzymes are, but without limitation, endoglucanases, beta-glucosidases, cellobiohydrolases, beta-xylosidases, endo(xylo)glucanases or endoxylanases. In an even more preferred embodiment, the cellulolytic enzymes are selected from endoglucanase, beta-glucosidase, cellobiohydrolase, beta-xylosidase, xyloglucanase, xylanase, arabinofuranosidase or any combination thereof.

The term "endoglucanase" or "EG" refers to a group of cellulase enzymes classified as E.C. 3.2.1.4. These enzymes hydrolyse the internal β-1,4 glycosidic bonds of cellulose.

The term "cellobiohydrolase" (EC 3.2.1.91 and EC 3.2.1.176) refers to a protein that catalyzes the hydrolysis of cellulose to cellobiose via exoglucanase activity, sequentially releasing cellobiose molecules from the reducing or non-reducing ends of cello-oligosaccharides.

The term "beta-glucosidase" (E.C. 3.2.1.21) as used herein refers to an enzyme that catalyzes the hydrolysis of a sugar dimer, including but without limitation, cellobiose, with the release of a corresponding sugar monomer, used for, but without limitation, ethanol synthesis. The enzyme beta-glucosidase acts on the β1→4 bridges linking two molecules of glucose or substituted glucose (that is, the disaccharide cellobiose). It is an exocellulase with specificity for a variety of beta-D-glucoside substrates. It catalyzes the hydrolysis of terminal non-reducing residues on beta-D-glucosides with the release of glucose.

The term "xylanase" refers to an enzyme that catalyses the endohydrolysis of 1,4-beta-D-xylosidic bonds in xylans.

The term "β-xylosidase" (EC 3.2.1.37) refers to a protein that hydrolyses short 1,4-β-D-xylo-oligomers to xylose.

The term "xyloglucanase" refers to a specific enzyme of xyloglucan able to catalyse the solubilisation of xyloglucan in oligosaccharides but does not show substantial cellulolytic activity.

The term "arabinofuranosidase" (EC 3.2.1.55) refers to the enzyme that catalyzes the hydrolysis of terminal non-reducing alpha-L-arabinofuranoside residues in alpha-L-arabinosides.

As stated above, PMOs and cellulolytic enzymes comprised in the composition of the invention may derive from any microorganism capable of producing cellulolytic enzymes. In an even more preferred embodiment of the composition of the invention, the PMO enzyme(s) and the cellulolytic enzymes are an enzymatic mixture secreted by *Myceliophthora thermophila*, more preferably *M. thermophila* strain C1. *Myceliophthora thermophila* strain may be a naturally occurring strain or a mutant strain which has been modified, for instance, to overexpress one or more of the secreted enzymes or to overexpress mutant enzymes with improved properties. This means that, preferably, the composition of the invention is an enzymatic mixture secreted by *Myceliophthora thermophila* which comprises PMOs and cellulolytic enzymes and further comprising a nickel cation. PMOs and cellulolytic enzymes may be naturally occurring in the microorganism which secretes them (i. e. wild type or native proteins), or may be proteins encoded by polynucleotides artificially introduced in the genome of said microorganism. Thus, these enzymes may be homologous (native) or heterologous (foreign) to the microorganism secreting them. Also, they can be recombinant proteins modified to improve one or more properties of the enzyme, or may be a combination of wild type proteins and recombinant proteins.

The term "secreted" or "expressed" includes any stage involved in the production of the polypeptide that includes, but without limitation, transcription, post-transcriptional modification, translation, post-translational modification, and secretion of a functional polypeptide to the culture media.

The *Myceliophthora thermophila* cell may be cultured in a suitable nutrient medium, solid or liquid, for the production of PMOs and cellulolytic enzymes, using procedures well known in the state of the art. For example, the cell may be cultured in a flask with agitation or by small or large scale fermentation (including continuous, discontinuous or batch fermentation, with discontinuous, fed batch or solid state feeding) performed in a laboratory or industrial bioreactor in a suitable medium and under conditions that enable expression and/or isolation of PMOs and cellulolytic enzymes. The culture takes place in a suitable nutrient medium comprising sources of carbon and nitrogen and inorganic salts, using the procedures known in the state of the art. PMO and cellulolytic enzymes are secreted into the nutrient medium and may be directly recovered from the same.

PMOs and cellulolytic enzymes may be recovered from the medium using procedures known in the state of the art. For example, they may be recovered from the nutrient medium by conventional procedures including, but without limitation, centrifugation, filtration, extraction, spray drying, evaporation or precipitation. These enzymes may be purified by a variety of procedures known in the state of the art including, but without limitation, chromatography (for example ion exchange, affinity, hydrophobic, chromatofocusing, and size exclusion), electrophoretic procedures (for example preparative isoelectric focusing), differential solubility (for example ammonium sulphate precipitation), SDS-PAGE or extraction.

Another aspect of the invention refers to the use of the composition of the invention for the degradation of cellulosic biomass.

The term "cellulosic biomass" means the biodegradable fraction of the products, residues and remains of biological origin from agriculture (including plant substances such as crop residues and animal substances), forestry (such as wood resources) and related industries that include fisheries and aquaculture, as well as the biodegradable fraction of industrial and urban waste such as municipal solid waste or paper residues. In a preferred embodiment, the cellulosic biomass is straw or the organic fraction of municipal solid waste. In a more preferred embodiment, the cellulosic biomass is plant biomass, preferably selected from the list consisting of: biomass rich in fermentable sugars such as sugar cane; starch biomass, for example wheat grain or straw; corn or corn straw or corn fiber or corn grain or corn stover; or barley grain or straw; or sorghum grain or straw. The biomass may also be rice, grass, shrubs, bagasse, etc.

The composition of the invention may be used in the production of monosaccharides, disaccharides and polysaccharides as chemical or fermentation raw materials for the production of ethanol, butanol, plastics, alkanes, alkenes and other intermediates or products from biomass. Thus, in a preferred embodiment, the degradation of cellulosic biomass takes place in a bioproduct production process.

The term "bioproduct" or "biobased products" refers to materials, chemical products and energy derived from renewable biological resources. Examples of bioproducts are, but without limitation, hydrocarbon compounds in different forms such as aliphatic (saturated, unsaturated, cyclic) or aromatic compounds such as alkanes, alkenes, alkynes, cyclic forms of these compounds or aromatic hydrocarbons; oxygenated substances such as alcohols (such as ethanol, butanol, sorbitol), ethers, aldehydes, ketones or carboxylic acids; nitrogenous substances such as amines, amides, nitro compounds or nitriles; halogenated substances such as halides; organic acids (such as lactic acid, acrylic acid, acetic acid, succinic acid, glutamic acid, citric acid or propionic acid). The term "bioproducts" also includes any combination of the compounds above, compounds additionally derived from the compounds above via any type of physical, chemical or biological treatment, polymers of the compounds above, compounds described above substituted by any group or functional element in one or more of its forms joined and branched with the compounds described above.

Ethanol may be produced through enzymatic degradation of biomass and the conversion of the released saccharides to ethanol. This type of ethanol is often called bioethanol. It may be used as a fuel additive or extender in blends of less than 1% up to 100% (a fuel substitute). In a more preferred embodiment, the bioproduct is a biofuel. In an even more preferred embodiment, the biofuel is bioethanol or butanol.

The term "biofuel" as used herein refers to a hydrocarbon or one of its mixtures that may be used as a fuel and is obtained using fermentable biomass as the starting material. Examples of biofuels include, but without limitation, ethanol or bioethanol, butanol or biobutanol and biodiesel.

The term "bioethanol" refers to an alcohol prepared by fermentation from fermentable biomass such as carbohydrates produced in sugar or starch crops such as corn or sugarcane.

The term "butanol" refers to a primary alcohol with a 4-carbon structure and the chemical formula $C_4H_9OH$. Its isomers include isobutanol, 2-butanol, and tert-butanol. Butanol has more than two carbon atoms and has significant solubility in water. n-Butanol occurs as a minor product of the fermentation of sugars and other carbohydrates.

The predominant polysaccharide in the primary cell wall of plant biomass is cellulose, the second most abundant is hemicellulose and the third, depending on the biomass in question, may be pectin. The secondary cell wall, produced after the cell has stopped its growth, also contains polysaccharides and is reinforced via polymeric lignin covalently cross-linked with hemicellulose. Cellulose is a homopolymer of anhydrocellobiose and so is a linear beta-(1-4)-D-glucan, whereas hemicellulose includes a variety of compounds such as xylans, xyloglucans, arabinoxylans, and mannans in complex branched structures with a range of substituents. Although generally polymorphous, cellulose is principally found in plant tissue as a crystalline insoluble matrix of parallel chains of glucan. Hemicelluloses normally bind together via hydrogen bonds to cellulose as well as to other hemicelluloses, which helps to stabilise the cell wall matrix. The composition of the invention may be used to degrade the cellulose component of biomass substrate.

Thus, another aspect of the invention refers to a process for producing fermentable sugars, hereinafter "first method of the invention", comprising:

a. Incubating cellulosic biomass with the composition of the invention, and
b. Recovering the fermentable sugars obtained after the incubation of step (a).

In the present invention, the nickel cation may be present in the bioreactor wherein the incubation step (a) is being performed and/or may be added to the enzymatic mixture before the cellulosic biomass saccharification step and/or during the same. Thus, in one embodiment of the present invention the nickel cation is added to the enzymatic mixture comprising PMOs and cellulolytic enzymes prior to its use in said step, preferably during the storage stage of the enzymatic mixture. This is advantageous for enhancing the stability of the PMOs in the composition. Alternatively or additionally to this embodiment, the nickel cation is added during the saccharification step, that is, at the same time or after the enzymatic mixture comprising PMOs and cellulolytic enzymes is put in contact or incubated with the cellulosic biomass.

Thus, another aspect of the invention refers to a process for producing fermentable sugars, hereinafter "second method of the invention", comprising:
a. Incubating cellulosic biomass with an enzymatic mixture comprising cellulolytic enzymes and at least one polysaccharide monooxygenase enzyme,
b. Adding a nickel cation to the incubation of step (a), and
c. Recovering the fermentable sugars obtained.

In a preferred embodiment of the second method of the invention, the PMO enzyme is selected from PMO1, PMO2, PMO3 or any combination thereof. In a more preferred embodiment, the PMO is PMO1 and/or PMO2. In an even more preferred embodiment, the PMO is PMO1 and PMO2.

In another preferred embodiment of the second method of the invention, the cellulolytic enzymes are selected from endoglucanase, beta-glucosidase, cellobiohydrolase, beta-xylosidase, xyloglucanase, xylanase, arabinofuranosidase or any combination thereof.

In a more preferred embodiment of the second method of the invention, the enzymatic mixture used in step (a) is an enzymatic mixture secreted by *M. thermophila*.

In another preferred embodiment of the second method of the invention, the nickel cation is added in step (b) at a concentration of more than 0.0001 mM and less than 50 mM, preferably between 0.001 and 20 mM, more preferably between 0.001 and 5 mM, even more preferably between 0.05 and 5 mM and even more preferably between 0.05 and 0.5 mM. In an even more preferred embodiment, the nickel cation is added in step (b) at a concentration between 0.075 and 0.125 mM, even more preferably the nickel cation is added in step (b) at a concentration of 0.125 mM.

In a more preferred embodiment of the second method of the invention, the nickel cation is added in step (b) in the form of a salt selected from nickel sulphate, nickel chloride, nickel nitrate, nickel acetate or nickel hydroxide, or any combination thereof.

The term "fermentable sugar" as used herein refers to simple sugars (monosaccharides, disaccharides and short oligosaccharides) such as glucose, xylose, arabinose, galactose, mannose, rhamnose, sucrose or fructose, among others. A fermentable sugar is any that may be used or fermented by a microorganism.

Degradation or hydrolysis of biomass to fermentable sugars, a process known as "saccharification", through the use of the composition of the invention, may be followed by a fermentation process in which fermentable sugars obtained are used in order to finally obtain a bioproduct such as bioethanol.

Thus, another aspect of the present invention refers to a process for producing a bioproduct from cellulosic biomass, hereinafter "third method of the invention", comprising:
a. Incubating cellulosic biomass with the composition of the invention,
b. Fermenting the fermentable sugars obtained after the incubation of step (a) with at least one fermenting microorganism, and
c. Recovering the bioproduct obtained after the fermentation step (b).

Another aspect of the invention refers to a process for producing a bioproduct from cellulosic biomass, hereinafter "fourth method of the invention", comprising:
a. Incubating cellulosic biomass with an enzymatic mixture comprising cellulolytic enzymes and at least one polysaccharide monooxygenase enzyme,
b. Adding a nickel cation to the incubation of step (a),
c. Fermenting the fermentable sugars obtained with at least one fermenting microorganism, and
d. Recovering the bioproduct obtained after the fermentation step (c).

In a preferred embodiment of the fourth method of the invention the PMO enzyme is selected from PMO1, PMO2, PMO3 or any combination thereof. In a more preferred embodiment, the PMO is PMO1 and/or PMO2. In an even more preferred embodiment, the PMO is PMO1 and PMO2.

In another preferred embodiment of the fourth method of the invention, the cellulolytic enzymes are selected from endoglucanase, beta-glucosidase, cellobiohydrolase, beta-xylosidase, xyloglucanase, xylanase, arabinofuranosidase or any combination thereof.

In a more preferred embodiment of the fourth method of the invention, the enzymatic mixture used in step (a) is an enzymatic mixture secreted by *M. thermophila*.

In another preferred embodiment of the fourth method of the invention, the nickel cation is added in step (b) at a concentration of more than 0.0001 mM and less than 50 mM, preferably between 0.001 and 20 mM, more preferably between 0.001 and 5 mM, even more preferably between 0.05 and 5 mM and even more preferably between 0.05 and 0.5 mM. In an even more preferred embodiment, the nickel cation is added in step (b) at a concentration between 0.075 and 0.125 mM, even more preferably the nickel cation is added in step (b) at a concentration of 0.125 mM.

The term "adding a nickel cation", as used in the present invention, refers to an automated or manual nickel addition to the enzymatic mixture. In the second and fourth method of the invention, this addition may be performed at the beginning of the incubation of step (a) and/or during said incubation process (at any moment before the hydrolysis or saccharification step ends).

These preferred nickel cation concentrations should be maintained during all the incubation step (a) (saccharification step) of the first, second, third and fourth method of the invention, so that in another preferred embodiment these four methods further comprise an additional step consisting of the supplementation, one or more times (as often as necessary), of the reaction being performed under step (a) with a nickel cation to maintain the concentration of said cation at more than 0.0001 mM and less than 50 mM, preferably between 0.001 and 20 mM, more preferably between 0.001 and 5 mM, even more preferably between 0.05 and 5 mM and even more preferably between 0.05 and 0.5 mM. In an even more preferred embodiment, to maintain the concentration of said cation at a concentration between 0.075 and 0.125 mM, even more preferably at a concentration of 0.125 mM.

In a more preferred embodiment of the fourth method of the invention, the nickel cation is added in step (b) in the form of a salt selected from nickel sulphate, nickel chloride, nickel nitrate, nickel acetate or nickel hydroxide, or any combination thereof.

In another preferred embodiment of the third and fourth method of the invention, the bioproduct is biofuel, more preferably the biofuel is bioethanol or butanol.

A method of pre-treating biomass is frequently required in order to increase the access of the enzymes to their substrates and consequently efficient hydrolysis. Pre-treatment uses various techniques that include, but without limitation, chemical treatment (for example explosion of the fibre with ammonium or exposure to a solvent), physical treatment (for example explosion with steam at elevated temperatures), mechanical treatment (for example, grinding or milling), biological treatment, or any of their combinations, to alter the structure of the cellulosic biomass and make the cellulose more accessible. Thus, the first, second, third and/or fourth method of the invention may comprise an additional step consisting of a pre-treatment process of the cellulosic biomass prior to the incubation step (a). In general, a pre-treatment process will result in the components of the cellulosic material being more accessible for the subsequent steps or being more digestible by the enzymes after treatment in the absence of hydrolysis. Pre-treatment may be chemical, physical, mechanical or biological pre-treatment, or any mixture of these.

The term "fermenting or fermentation" as used herein refers to a process of biological transformation caused by the activity of some microorganisms in which sugars such as glucose, fructose and sucrose are converted into ethanol. The microorganisms used in this way are fermenting microorganisms that have the capacity to ferment, such as yeasts of the genera *Saccharomyces, Pichia* or *Kluyveromyces*, preferably *Saccharomyces cerevisiae*, either natural strains or those genetically modified for the conversion of pentoses.

The term "recovery" as used herein refers to the recovery of the fermentable sugars obtained after the incubation step of the first and second procedures of the invention or of the bioproduct obtained after the fermentation step of the third and fourth procedures of the invention. Recovery can be performed via any procedure known in the state of the art, including mechanical or manual methods.

Before (that is in step (a)) and/or simultaneously with the fermentation step of the third and fourth method of the invention, the biomass, preferably pre-treated biomass, is hydrolysed to degrade the cellulose and hemicellulose into sugars and/or oligosaccharides. The solid content during the hydrolysis may be, but without limitation, between 10-30% of the total weight, preferably between 15-25% of the total weight, more preferably between 18-22% of the total weight. Hydrolysis is carried out as a process in which biomass, preferably pre-treated biomass, is incubated with the composition of the invention and thus forms the hydrolysis solution. The appropriate processing time, temperature and pH conditions may be easily determined by an expert in the field. Preferably, this hydrolysis is performed at a temperature of between 25° C. and 60° C., preferably between 40° C. and 60° C., specifically around 50° C. The process is preferably performed at a pH in the interval between 4 to 6, preferably between 4.5 and 5.5, specifically around pH 5.2. The hydrolysis is preferably performed in a time of between 12 and 144 hours, preferably between 16 and 120 hours, more preferably between 24 and 96 hours, and even more preferably between 32 and 72 hours.

Hydrolysis and fermentation of the third and fourth method of the invention may be carried out simultaneously (SSF process) or sequentially (SHF process), i. e. steps (a) and (b) of the third method of the invention and steps (a) and (c) of the fourth method of the invention may be performed simultaneously or sequentially. In accordance with the invention, the hydrolysed, and preferably pre-treated biomass, is fermented by at least one fermenting microorganism capable of fermenting fermentable sugars such as glucose, xylose, mannose and galactose, directly or indirectly into the desired fermentation product. Fermentation is preferably performed in a time of between 8 and 96 hours, preferably between 12 and 72 hours and more preferably between 24 and 48 hours. In another preferred embodiment, the fermentation is performed at a temperature of between 20° C. and 40° C., preferably between 26° C. and 34° C., in particular of around 32° C. In another preferred embodiment, the pH is between 3 and 6 units, preferably between 4 and 5. For ethanol fermentation, a yeast of the species *Saccharomyces cerevisiae* is preferred, preferably strains that are resistant to high levels of ethanol, up to, for example between 5% and 7% by volume of ethanol or higher such as between 10% and 15% by volume of ethanol.

As explained above, the presence of a nickel cation in enzymatic mixtures comprising PMOs, as proposed by the present invention, leads to an increased PMO activity and stability. The term "increase in the activity" as used in this invention refers to the increase in yield (preferably amount) of a reaction product, for example of a fermentable sugar, produced when a particular component present during the reaction (a nickel cation) leads to a higher production of the product by the enzymatic cocktail comprising PMOs compared to a reaction carried out under the same conditions and with the same substrate but in the absence of the component in question. The term "increase in the stability" refers to the maintenance or retention of the properties (e. g. activity) and structure of an enzyme, particularly of a PMO enzyme, in the presence of a particular component (a nickel cation) during the reaction or storage, as the physical conditions, such as temperature or other factors, such as pH, deviate from the optimum values for the enzyme. In a preferred embodiment, the term "increase in the stability" means "increase in the thermal stability".

Another aspect of the invention refers to a process for the preparation of the composition of the invention comprising adding a nickel cation to an enzymatic mixture comprising at least one PMO enzyme, hereinafter "fifth method of the invention".

In a preferred embodiment of the fifth method of the invention, the PMO enzyme is selected from PMO1, PMO2, PMO3 or any combination thereof.

In another preferred embodiment of the fifth method of the invention, the enzymatic mixture further comprises cellulolytic enzymes selected from endoglucanase, beta-glucosidase, cellobiohydrolase, beta-xylosidase, xyloglucanase, xylanase, arabinofuranosidase or any combination thereof.

In a more preferred embodiment of the fifth method of the invention, the enzymatic mixture is an enzymatic mixture secreted by *M. thermophila*.

In another preferred embodiment of the fifth method of the invention, the nickel cation is added at a concentration of more than 0.0001 mM and less than 50 mM, preferably between 0.001 and 20 mM, more preferably between 0.001 and 5 mM, even more preferably between 0.05 and 5 mM and even more preferably between 0.05 and 0.5 mM. In an even more preferred embodiment, the nickel cation is added at a concentration between 0.075 and 0.125 mM, even more preferably at a concentration of 0.125 mM.

In a more preferred embodiment of the fifth method of the invention, the nickel cation is added in the form of a salt selected from nickel sulphate, nickel chloride, nickel nitrate, nickel acetate or nickel hydroxide, or any combination thereof.

The composition of the invention can be in liquid form or in the form of a dry composition. For example, the composition may be in granular or microgranular form. The enzymes to be included in the composition may be stabilised in accordance with procedures known in the state of the art.

Throughout the description and the claims, the word "comprise" and its variants are not intended to exclude other technical characteristic, additives, components or steps. For an expert in the field, other objects, benefits and characteristics of the invention will be revealed, partly from the description and partly from the practice of the invention. The following examples and figures are provided for illustration purposes only and are not intended to be limiting of this invention.

EXAMPLES

Example 1. Effect of Nickel Ion Concentration on Glucose Yield Released by C1 Enzyme Composition The effect of nickel (II) ions on the saccharification performance of cellulase preparation from C1 on pretreated corn stover (hereinafter PCS) was evaluated according to the procedures described below. The cellulase preparation is designated hereinafter as the "C1 composition".

The enzymatic mixture, "C1 composition", produced by *Myceliophthora thermophila* C1 was obtained following the procedures previously described (Verdoes et al., 2007, *Ind. Biotechnol.* 3 (1) and Visser et al., 2011, *Ind. Biotechnol.*, 7 (3)), using an industrial platform for enzyme production based on *M. thermophila* C1 developed by Dyadic Netherlands.

PCS obtained according to Nguyen et al. (1998, *Appl. Biochem. Biotechnol.* 70-72) was used as substrate for the hydrolysis reaction. The compositional analysis was performed using the procedures of NREL as "Standard Biomass AnalyticalProcedures". This biomass was neutralized, lyophilized and milled.

C1 cellulase composition of *Myceliophthora thermophila* was used as the cellulase preparation. The hydrolysis of PCS was conducted in 10 ml plastic tubes with a reaction volume of 3.0 ml at 20% total solids adding 10 mg of protein per gram of glucan at 0-50 mM Nickel sulphate hexahydrated. Tubes were mixed and incubated at 50° C., pH 5, 250 rpm for 72 h. All experiments were performed at least in duplicate.

After hydrolysis, samples were filtered using a 0.22 μm nylon filter and filtrates were analyzed for sugar content as described below. The sugar concentrations of samples, diluted to appropriate concentrations in 5 mM $H_2SO_4$, were measured using a 4.6×250 mm AMINEX® HPX-87H column (Bio-Rad Laboratories, Inc., Hercules, Calif., USA) by elution with 5 mM $H_2SO_4$ at a flow rate of 0.6 ml per minute, and quantitated by integration of the glucose, cellobiose and xylose signals from refractive index detection (CHEMSTATION®, AGILENT® 1100 HPLC, Agilent Technologies, Santa Clara, Calif., USA) calibrated by pure sugar samples.

Figure 1:
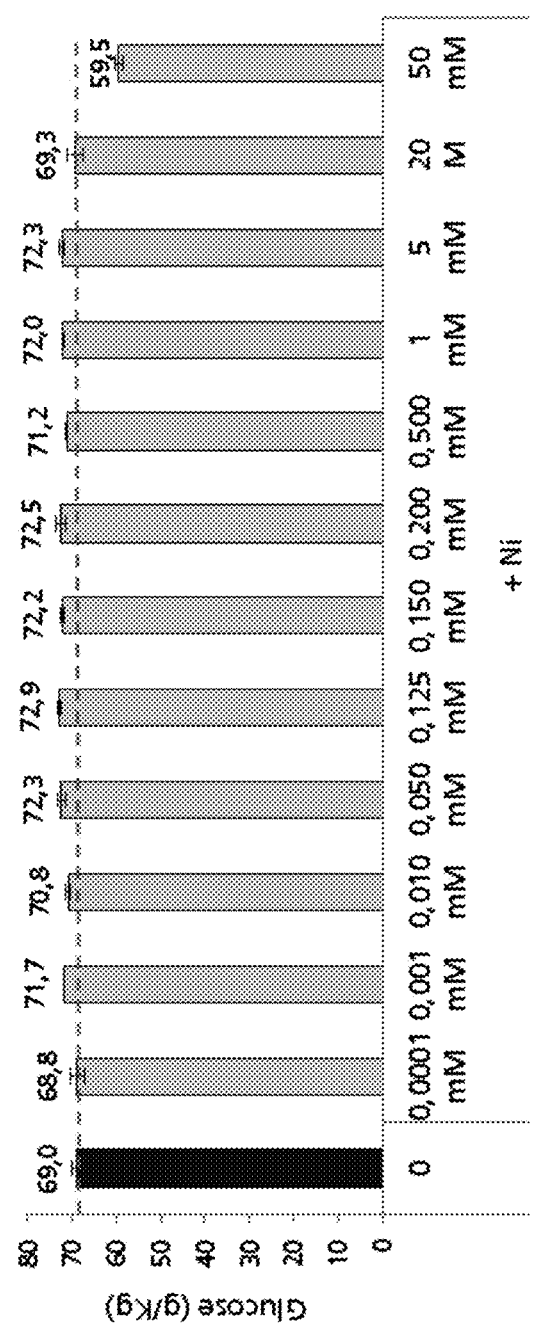
FIG. 1. Improvement of the yield of glucose (g/kg) by the enzymatic cocktail produced by *M. thermophila* C1 in the absence (0) or in the presence of different nickel concentrations (mM) on pretreated corn stover (PCS).

FIG. 1 shows the effect of different concentrations of nickel (mM) on glucose release (g/Km). It can be seen that the optimum nickel concentration was 0.125 mM (125 μM).

Example 2. Comparison of Different Nickel Salts on Glucose Release

Different nickel salts were compared following the same procedure described in the example 1. Nickel was added as nickel sulphate hexahydrated, nickel chloride, nickel acetate tetrahydrated, nickel nitrate hexahydrated and nickel hydroxide to a final concentration of nickel ion of 125 μM.

Figure 2:
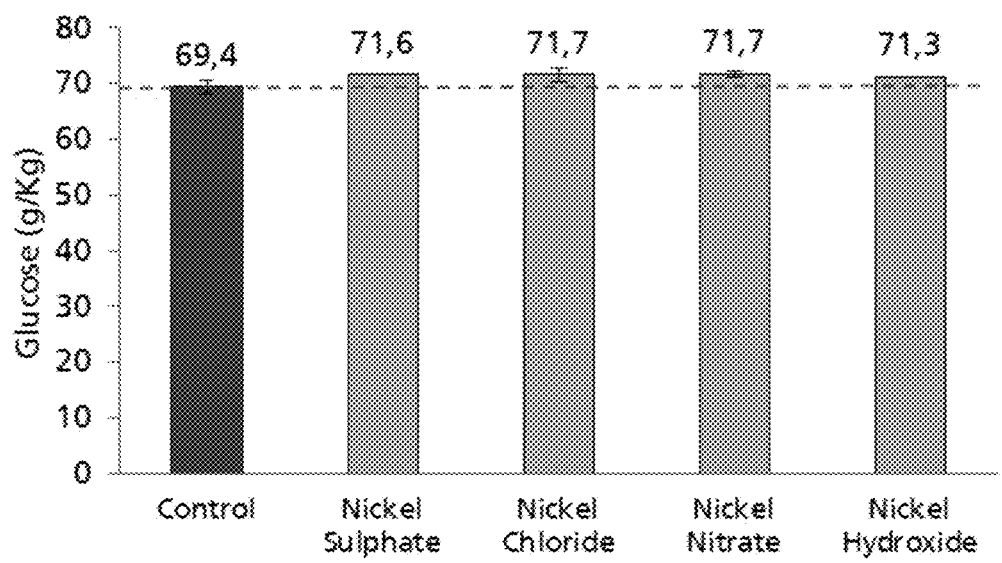
FIG. 2. Improvement of the yield of glucose and xylose (g/kg) released from pretreated corn stover biomass by the enzymatic cocktail produced by *M. thermophila* C1 in the absence (Control) or in the presence of different nickel salts.
Figure 2:
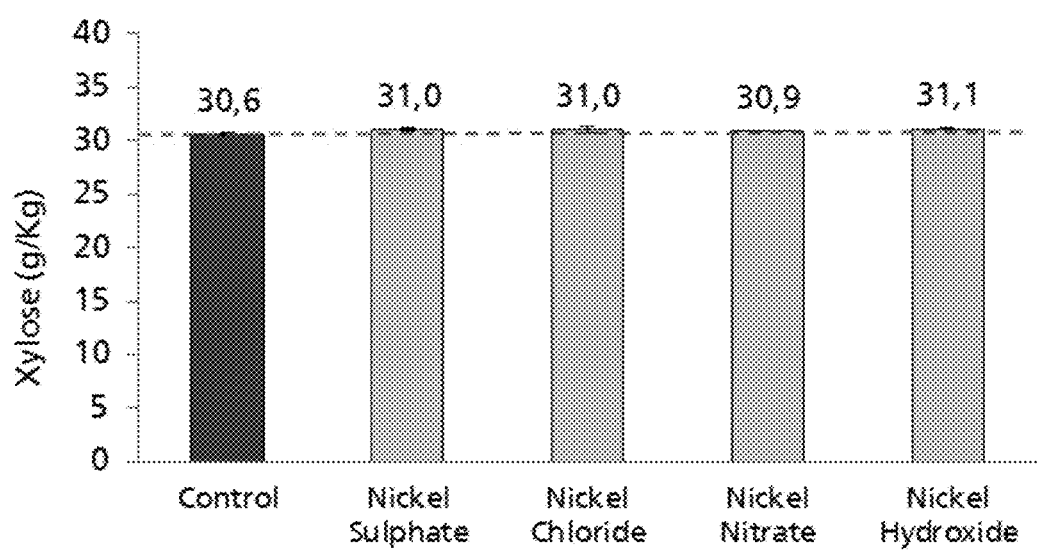

FIG. 2 shows the effect of nickel salts supplementation on glucose and xylose release. The supplementation of Nickel improved glucose release but xylose yield was not significantly affected. All nickel salts used produced the same glucose release improvement. The same effect was also obtained with nickel acetate tetahydrated (data not shown).

Example 3. Evaluation of Nickel Supplementation on Polysaccharide Monooxygenase Activity The effect of nickel supplementation on several cellulolytic enzymes was compared following the same procedure described in the example 1. Here C1 composition was replaced by an enzymatic mixture containing the main celulases, where an endoglucanase, a beta-glucosidase, two kind of cellobiohydrolases (Type I and II) and two examples of polysaccharide monooxygenases, all of them obtained from *Myceliophthora thermophila*, were included in the cellulase preparation. The final dosage of the enzymatic mix was 8.5 mg of protein per gram of glucan.

Figure 3:
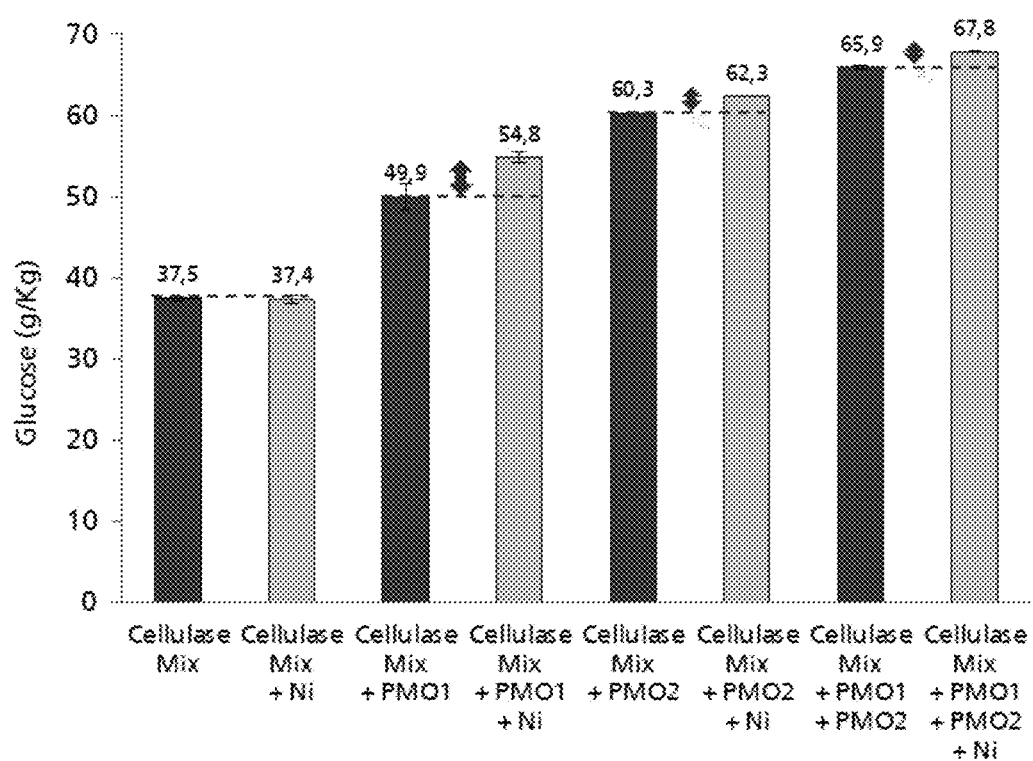
FIG. 3. Improvement in the yield of glucose (g/kg) over biomass by a defined enzyme composition including endoglucanase, beta-glucosidase, cellobiohydrolases (Cellulase Mix) in the absence or in the presence of polysaccharide monooxygenases (PMO1 and/or PMO2) and in the absence or in the presence of nickel.

The FIG. 3 shows the comparison of four defined compositions: (1) defined composition with endoglucanase, beta-glucosidase, both cellobiohydrolases and without polysaccharide monooxygenases (cellulase mix), (2) defined composition with cellulase mix plus PMO1, (3) cellulase mix supplemented with PMO2 and (4) cellulase mix supplemented with PMO1 and PMO2.

Supplementation of nickel at 125 µM improved all defined compositions that contained polysaccharide monooxygenases (PMO1 or/and PMO2) but did not improve the defined composition without polysaccharide monooxygenases.

Example 4. Evaluation of Nickel Supplementation on Polysacharide Monooxygenase Stability Stability of different PMOs was evaluated with thermofluorescence assay on Na-acetate buffer 200 mM, pH 5.0 and different concentrations of nickel. Experimental conditions were a lineal gradient of temperature 23-95° C. (0.8° C./min). Detection signal was measured with fluorescence of SYPRO orange protein gel stain (Sigma-Aldrich, St. Louis, Mo., USA) with and without nickel at different concentrations (0-200 µM) added as nickel sulphate heptahydrated. Tm represents temperature values (° C.) at which 50% of the enzyme is denatured. PMO1 and PMO2 were obtained *Myceliophthora thermophila* while PMO3 was obtained from *Penicilium* sp.

As a general procedure to purify those PMOs, fungal cultures were centrifuged (21.000×g, 40 min, 5° C.) to obtain cellulase enriched supernatants that were applied on a HiLoad 26/10 Q-Sepharose High Performance (53 ml) column pre-equilibrated with 50 mM Tris-HCl buffer, pH 7.0. After washing with the same buffer the bound protein was eluted with a 0-0.5 M NaCl gradient with a flow rate of 8 ml/min. PMOs enriched fractions were collected and loaded into a HiLoad 26/10 Phenyl-Sepharose High Performance column (53 ml) pre-equilibrated with 100 mM Na-Phosphate buffer, pH 7.0, 1M $(NH_4)_2SO_4$. The protein was eluted with a linear gradient of 100 mM Na-Phosphate buffer, pH 7.0 at a flow rate of 8 ml/min. Enriched fractions could also need an extra purification step with a HiPrep 26/10 desalting column equilibrated with 50 mM Na-Phosphate buffer, pH 7.0 or even a HiLoad 16/600 Superdex 75 pg (120 ml), this column was equilibrated with 50 mM Na-Phosphate buffer, pH 7.0.

Figure 4:
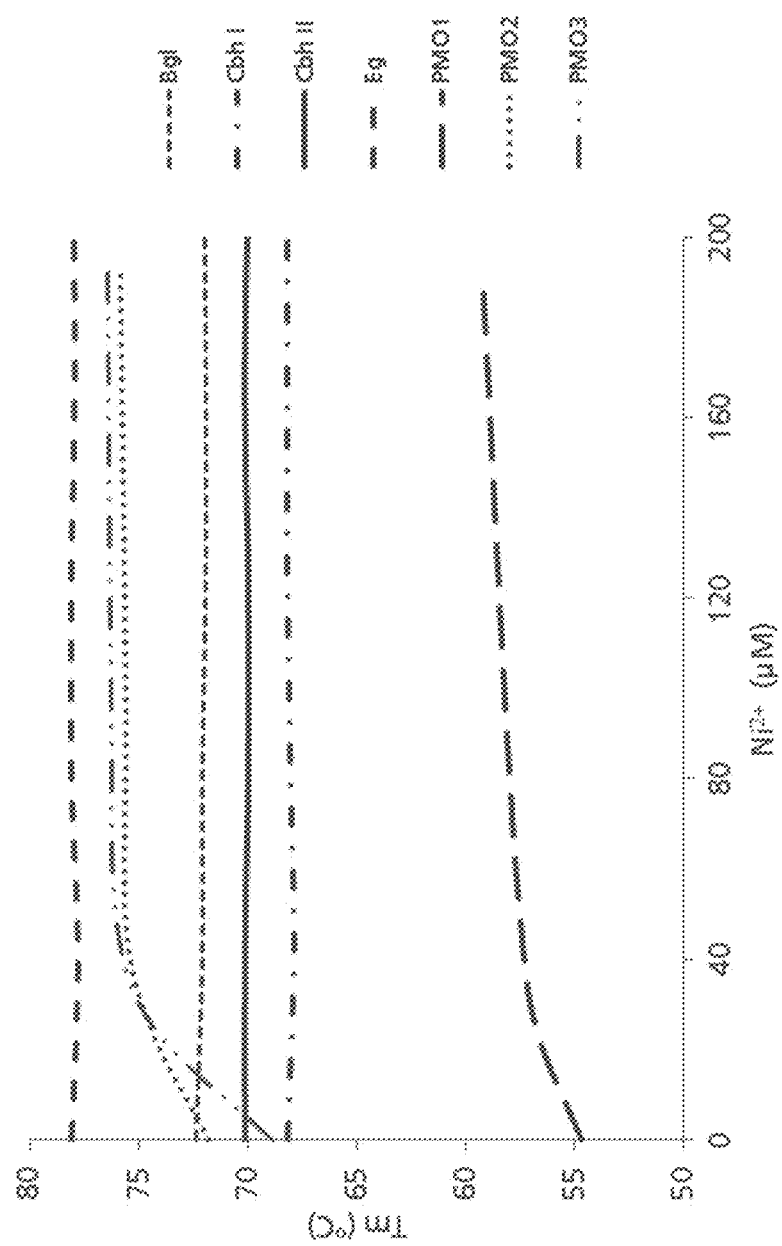
FIG. 4. Stability of several cellulolytic enzymes in the presence of different nickel concentrations (0). This figure represents the Tm values (° C.) at which 50% of the enzyme is denaturalizated. As the nickel concentration increases, PMOs become more stable as shown by the Tm increase indicating that a higher temperature is required to denature the PMO. Thermostability of other celulolytic enzymes is not affected by nickel addition.

FIG. 4 shows that average Tm of PMOs increased about 5° C. when Ni concetration was added. This indicates that as the nickel concentration increases, PMOs become more stable as shown by the Tm increase, indicating that a higher temperature is required to denature the PMO when nickel is present. This figure also evidences that thermostability of other celulolytic enzymes is not affected by nickel addition.

Example 5. Comparison of Nickel and Other Divalent Salts on the Saccharification of Pretreated Corn Stover Nickel supplementation was compared with the supplementation of other divalent ions like magnesium or manganese at different concentrations following the same procedure as described in the example 1.

Nickel was added as nickel acetate tetrahydrated, magnesium as magnesium sulphate heptahydrated and manganese sulphate monohydrated.

Figure 5:
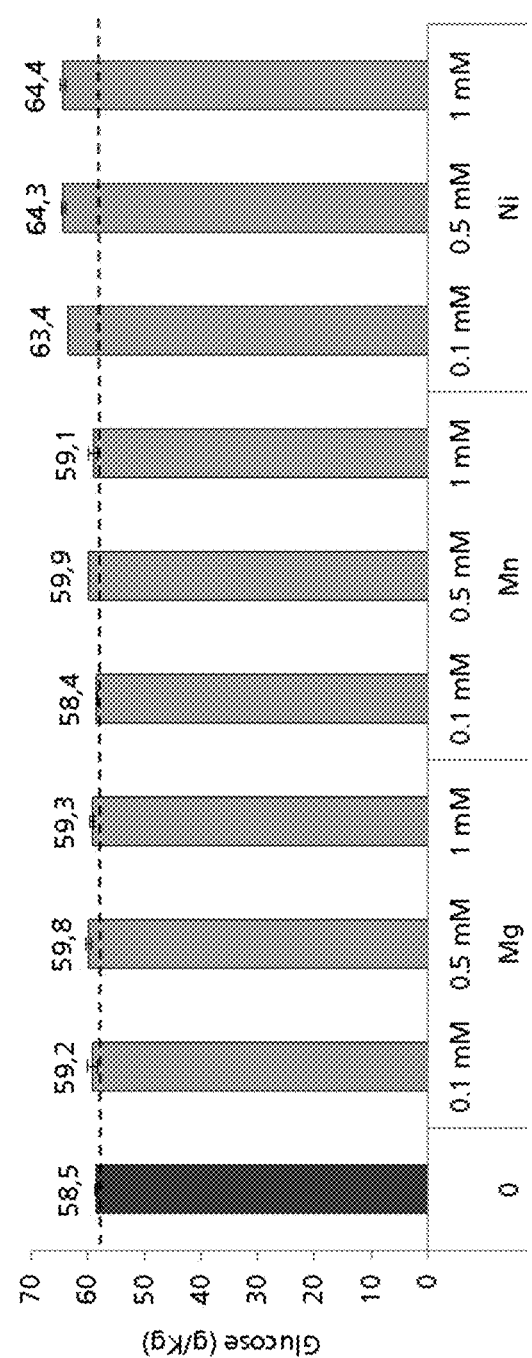
FIG. 5. Improvement in the yield of glucose (g/kg) by the enzymatic cocktail produced by *M. thermophila* C1 in the absence (0) or in the presence of different concentrations (mM) of different divalent cations over biomass.

The supplementation of nickel enhanced the glucose release (g/Kg) more than other divalent ions (FIG. 5).

The invention claimed is:

1. A composition comprising at least one isolated and purified polysaccharide monooxygenase enzyme and a nickel cation, wherein the nickel cation is present at a concentration between 0.05 and 0.5 mM.

2. The composition according to claim 1 wherein the nickel cation is in the form of a salt selected from the group consisting of: nickel sulphate, nickel chloride, nickel nitrate, nickel acetate, nickel hydroxide, and any combination thereof.

3. The composition according to claim 1 wherein the polysaccharide monooxygenase enzyme is selected from the group consisting of: PMO1 comprising SEQ ID NO: 1, PMO2 comprising SEQ ID NO: 2, PMO3 comprising SEQ ID NO: 3, and any combination thereof.

4. The composition according to claim 1 wherein the composition further comprises cellulolytic enzymes selected from the group consisting of: endoglucanase, beta-glucosidease, cellobiohydrolase, beta-xylosidase, xyloglucanase, xylanase, arabinofuranosidase and any combination thereof.

5. The composition according to claim 4 wherein the polysaccharide monooxygenase enzyme and the cellulolytic enzymes are an enzymatic mixture secreted by *Myceliophthora thermophila*.

6. A process for producing fermentable sugars comprising:
   a. Incubating cellulosic biomass with the composition according to claim 1, and
   b. Recovering the fermentable sugars obtained after the incubation of step (a).

7. A process for producing fermentable sugars comprising:
   a. Incubating cellulosic biomass with an enzymatic mixture comprising cellulolytic enzymes and at least one isolated and purified polysaccharide monooxygenase enzyme,
   b. Adding a nickel cation to the incubation of step (a) at a concentration between 0.05 and 0.5 mM, and
   c. Recovering the fermentable sugars obtained.

8. The process according to claim 7 wherein the polysaccharide monooxygenase enzyme is selected from the group consisting of: PMO1 comprising SEQ ID NO: 1, PMO2 comprising SEQ ID NO: 2, PMO3 comprising SEQ ID NO: 3 and any combination thereof.

9. The process according to claim 7 wherein the cellulolytic enzymes are selected from the group consisting of: endoglucanase, beta-glucosidase, cellobiohydrolase, beta-xylosidase, xyloglucanase, xylanase, arabinofuranosidase and any combination thereof.

10. The process according to claim 7 wherein the enzymatic mixture used in step (a) is an enzymatic mixture secreted by *Myceliophthora thermophila*.

11. The process according to claim 7 wherein the nickel cation is added in step (b) in the form of a salt selected from the group consisting of: nickel sulphate, nickel chloride, nickel nitrate, nickel acetate, nickel hydroxide, and any combination thereof.

12. A process for producing a bioproduct from cellulosic biomass comprising:
   a. Incubating cellulosic biomass with the composition according to claim 1,
   b. Fermenting the fermentable sugars obtained after the incubation of step (a) with at least one fermenting microorganism, and
   c. Recovering the bioproduct obtained after the fermentation step (b).

13. A process for producing a bioproduct from cellulosic biomass comprising:
   a. Incubating cellulosic biomass with an enzymatic mixture comprising cellulolytic enzymes and at least one isolated and purified polysaccharide monooxygenase enzyme,
   b. Adding a nickel cation to the incubation of step (a) at a concentration between 0.05 and 0.5 mM,
   c. Fermenting the fermentable sugars obtained with at least one fermenting microorganism, and
   d. Recovering the bioproduct obtained after the fermentation step (c).

14. The process according to claim 13 wherein the polysaccharide monooxygenase enzyme is selected from the group consisting of: PMO1 comprising SEQ ID NO: 1, PMO2 comprising SEQ ID NO: 2, PMO3 comprising SEQ ID NO: 3 and any combination thereof.

15. The process according to claim 13 wherein the cellulolytic enzymes are selected from the group consisting of: endoglucanase, beta-glucosidase, cellobiohydrolase, beta-xylosidase, xyloglucanase, xylanase, arabinofuranosidase and any combination thereof.

16. The process according to claim 13 wherein the enzymatic mixture used in step (a) is an enzymatic mixture secreted by *Myceliophthora thermophila*.

17. The process according to claim 13 wherein the nickel cation is added in step (b) in the form of a salt selected from the group consisting of: nickel sulphate, nickel chloride, nickel nitrate, nickel acetate, nickel hydroxide, and any combination thereof.

18. The process according to claim 12 wherein the bioproduct is biofuel.

19. The process according to claim 18 wherein the biofuel is bioethanol or butanol.

20. The process according to claim 13 wherein the bioproduct is biofuel.

* * * * *

SEQUENCE LISTING

```
<160> NUMBER OF SEQ ID NOS: 3

<210> SEQ ID NO 1
<211> LENGTH: 255
<212> TYPE: PRT
<213> ORGANISM: Myceliophthora thermophila

<400> SEQUENCE: 1

Met Tyr Arg Thr Leu Gly Ser Ile Ala Leu Leu Ala Gly Gly Ala Ala
1               5                   10                  15

Ala His Gly Ala Val Thr Ser Tyr Asn Ile Ala Gly Lys Asp Tyr Pro
            20                  25                  30

Gly Tyr Ser Gly Phe Ala Pro Thr Gly Gln Asp Val Ile Gln Trp Gln
        35                  40                  45

Trp Pro Asp Tyr Asn Pro Val Leu Ser Ala Ser Asp Pro Lys Leu Arg
    50                  55                  60

Cys Asn Gly Gly Thr Gly Ala Ala Leu Tyr Ala Glu Ala Ala Pro Gly
65                  70                  75                  80

Asp Thr Ile Thr Ala Thr Trp Ala Gln Trp Thr His Ser Gln Gly Pro
                85                  90                  95

Ile Leu Val Trp Met Tyr Lys Cys Pro Gly Asp Phe Ser Ser Cys Asp
            100                 105                 110

Gly Ser Gly Ala Gly Trp Phe Lys Ile Asp Glu Ala Gly Phe His Gly
        115                 120                 125

Asp Gly Thr Thr Val Phe Leu Asp Thr Glu Thr Pro Ser Gly Trp Asp
    130                 135                 140

Ile Ala Lys Leu Val Gly Gly Asn Lys Ser Trp Ser Ser Lys Ile Pro
145                 150                 155                 160

Asp Gly Leu Ala Pro Gly Asn Tyr Leu Val Arg His Glu Leu Ile Ala
```

```
                    165                 170                 175
Leu His Gln Ala Asn Asn Pro Gln Phe Tyr Pro Glu Cys Ala Gln Ile
                180                 185                 190

Lys Val Thr Gly Ser Gly Thr Ala Glu Pro Ala Ala Ser Tyr Lys Ala
            195                 200                 205

Ala Ile Pro Gly Tyr Cys Gln Gln Ser Asp Pro Asn Ile Ser Phe Asn
        210                 215                 220

Ile Asn Asp His Ser Leu Pro Gln Glu Tyr Lys Ile Pro Gly Pro Pro
225                 230                 235                 240

Val Phe Lys Gly Thr Ala Ser Ala Lys Ala Arg Ala Phe Gln Ala
                245                 250                 255

<210> SEQ ID NO 2
<211> LENGTH: 323
<212> TYPE: PRT
<213> ORGANISM: Myceliophthora thermophila

<400> SEQUENCE: 2

Met Lys Ser Phe Thr Leu Thr Thr Leu Ala Ala Leu Ala Gly Asn Ala
1               5                   10                  15

Ala Ala His Ala Thr Phe Gln Ala Leu Trp Val Asp Gly Val Asp Tyr
            20                  25                  30

Gly Ala Gln Cys Ala Arg Leu Pro Ala Ser Asn Ser Pro Val Thr Asp
        35                  40                  45

Val Thr Ser Asn Ala Ile Arg Cys Asn Ala Asn Pro Ser Pro Ala Arg
    50                  55                  60

Gly Lys Cys Pro Val Lys Ala Gly Ser Thr Val Thr Val Glu Met His
65                  70                  75                  80

Gln Gln Pro Gly Asp Arg Ser Cys Ser Ser Glu Ala Ile Gly Gly Ala
                85                  90                  95

His Tyr Gly Pro Val Met Val Tyr Met Ser Lys Val Ser Asp Ala Ala
            100                 105                 110

Ser Ala Asp Gly Ser Ser Gly Trp Phe Lys Val Phe Glu Asp Gly Trp
        115                 120                 125

Ala Lys Asn Pro Ser Gly Gly Ser Gly Asp Asp Tyr Trp Gly Thr
    130                 135                 140

Lys Asp Leu Asn Ser Cys Cys Gly Lys Met Asn Val Lys Ile Pro Ala
145                 150                 155                 160

Asp Leu Pro Ser Gly Asp Tyr Leu Leu Arg Ala Glu Ala Leu Ala Leu
                165                 170                 175

His Thr Ala Gly Ser Ala Gly Gly Ala Gln Phe Tyr Met Thr Cys Tyr
            180                 185                 190

Gln Leu Thr Val Thr Gly Ser Gly Ser Ala Ser Pro Pro Thr Val Ser
        195                 200                 205

Phe Pro Gly Ala Tyr Lys Ala Thr Asp Pro Gly Ile Leu Val Asn Ile
    210                 215                 220

His Ala Pro Leu Ser Gly Tyr Thr Val Pro Gly Pro Ala Val Tyr Ser
225                 230                 235                 240

Gly Gly Ser Thr Lys Lys Ala Gly Ser Ala Cys Thr Gly Cys Glu Ser
                245                 250                 255

Thr Cys Ala Val Gly Ser Gly Pro Thr Ala Thr Val Ser Gln Ser Pro
            260                 265                 270

Gly Ser Thr Ala Thr Ser Ala Pro Gly Gly Gly Gly Cys Thr Val
        275                 280                 285
```

```
Gln Lys Tyr Gln Gln Cys Gly Gly Gln Gly Tyr Thr Gly Cys Thr Asn
    290                 295                 300

Cys Ala Ser Gly Ser Thr Cys Ser Ala Val Ser Pro Pro Tyr Tyr Ser
305                 310                 315                 320

Gln Cys Val

<210> SEQ ID NO 3
<211> LENGTH: 284
<212> TYPE: PRT
<213> ORGANISM: Myceliophthora thermophila

<400> SEQUENCE: 3

His Tyr Ile Phe Gln Gln Leu Thr Thr Gly Gly Val Lys His Ala Val
1               5                   10                  15

Tyr Gln Tyr Ile Arg Lys Asn Thr Asn Tyr Asn Ser Pro Val Thr Asp
                20                  25                  30

Leu Thr Ser Asn Asp Leu Arg Cys Asn Val Gly Ala Thr Gly Ala Gly
            35                  40                  45

Thr Asp Thr Val Thr Val Arg Ala Gly Asp Ser Phe Thr Phe Thr Thr
    50                  55                  60

Asp Thr Pro Val Tyr His Gln Gly Pro Thr Ser Ile Tyr Met Ser Lys
65                  70                  75                  80

Ala Pro Gly Ser Ala Ser Asp Tyr Asp Gly Ser Gly Gly Trp Phe Lys
                85                  90                  95

Ile Lys Asp Trp Gly Ala Asp Phe Ser Ser Gly Gln Ala Thr Trp Thr
                100                 105                 110

Leu Ala Ser Asp Tyr Thr Ala Thr Ile Pro Glu Cys Ile Pro Pro Gly
            115                 120                 125

Asp Tyr Leu Leu Arg Ile Gln Gln Leu Gly Ile His Asn Pro Trp Pro
    130                 135                 140

Ala Gly Ile Pro Gln Phe Tyr Ile Ser Cys Ala Gln Ile Thr Val Thr
145                 150                 155                 160

Gly Gly Gly Ser Ala Asn Pro Gly Pro Thr Val Ser Ile Pro Gly Ala
                165                 170                 175

Phe Lys Glu Thr Asp Pro Gly Tyr Thr Val Asn Ile Tyr Asn Asn Phe
                180                 185                 190

His Asn Tyr Thr Val Pro Gly Pro Ala Val Phe Thr Cys Asn Gly Ser
            195                 200                 205

Gly Gly Asn Asn Gly Gly Ser Asn Pro Val Thr Thr Thr Thr
    210                 215                 220

Thr Thr Thr Arg Pro Ser Thr Ser Thr Ala Gln Ser Gln Pro Ser Ser
225                 230                 235                 240

Ser Pro Thr Ser Pro Ser Ser Cys Thr Val Ala Lys Trp Gly Gln Cys
                245                 250                 255

Gly Gly Gln Gly Tyr Ser Gly Cys Thr Val Cys Ala Ala Gly Ser Thr
            260                 265                 270

Cys Gln Lys Thr Asn Asp Tyr Tyr Ser Gln Cys Leu
    275                 280
```